US011273302B2

(12) United States Patent
Botzer et al.

(10) Patent No.: US 11,273,302 B2
(45) Date of Patent: *Mar. 15, 2022

(54) TISSUE CONDUCTION VELOCITY

(71) Applicant: BIOSENSE WEBSTER (ISRAEL) LTD., Yokneam (IL)

(72) Inventors: Lior Botzer, Timrat (IL); Amir Ben-Dor, Kibbutz Hamapil (IL); Yoram Chmiel, Aliso Viejo, CA (US); Aharon Turgeman, Zichron Ya'acov (IL); Liron Shmuel Mizrahi, Kiryat Bialik (IL); Noga Salomon, Karmiel (IL); Galia Givaty, Haifa (IL)

(73) Assignee: Biosense Webster (Israel) Ltd., Yokneam (IL)

(*) Notice: Subject to any disclaimer, the term of this patent is extended or adjusted under 35 U.S.C. 154(b) by 152 days.

This patent is subject to a terminal disclaimer.

(21) Appl. No.: 16/708,488

(22) Filed: Dec. 10, 2019

(65) Prior Publication Data

US 2020/0108243 A1  Apr. 9, 2020

Related U.S. Application Data

(63) Continuation of application No. 15/477,731, filed on Apr. 3, 2017, now Pat. No. 10,576,263.

(51) Int. Cl.
*A61N 1/36* (2006.01)
*A61N 1/00* (2006.01)
*A61B 5/0245* (2006.01)
*A61B 5/00* (2006.01)
*A61B 5/318* (2021.01)
(Continued)

(52) U.S. Cl.
CPC .............. *A61N 1/00* (2013.01); *A61B 5/0245* (2013.01); *A61B 5/318* (2021.01); *A61B 5/349* (2021.01); *A61B 5/6852* (2013.01); *A61N 1/36* (2013.01); *A61N 1/362* (2013.01); *A61N 1/3622* (2013.01); *A61N 1/36521* (2013.01); *A61N 1/3704* (2013.01); *A61N 1/3706* (2013.01); *A61B 5/0538* (2013.01); *A61B 5/062* (2013.01);
(Continued)

(58) Field of Classification Search
CPC .................................. A61N 1/36; A61N 1/362
USPC ......................................................... 600/508
See application file for complete search history.

(56) References Cited

U.S. PATENT DOCUMENTS 6,236,883 B1   5/2001   Ciaccio et al.
6,301,496 B1  10/2001   Reisfeld
(Continued)

OTHER PUBLICATIONS

Itoh, Taihei M.D., Ph.D., et al., "High Correlation of Estimated Local Conduction Velocity with Natural Logarithm of Bipolar Electrogram Amplitude in the Reentry Circuit of Atrial Flutter", Journal of Cardiovascular Electrophysiology, Apr. 2014, pp. 387-394, vol. 25, No. 4.

(Continued)

Primary Examiner — Nadia A Mahmood

(57) ABSTRACT

A method includes acquiring a bipolar signal from a first electrode and a second electrode contacting a first location and a second location, respectively, in a heart of a living subject. The method further includes acquiring a unipolar signal from the first electrode while in contact with the first location, and deriving from the bipolar signal and the unipolar signal a point in time at which the first location is generating the unipolar signal. The method also includes computing a metric for a conduction velocity of the unipolar signal at the first location based on a shape of the unipolar signal at the point in time.

8 Claims, 5 Drawing Sheets

(51) Int. Cl.
  *A61B 5/349* (2021.01)
  *A61N 1/362* (2006.01)
  *A61N 1/365* (2006.01)
  *A61N 1/37* (2006.01)
  *A61B 5/0538* (2021.01)
  *A61B 5/06* (2006.01)

(52) U.S. Cl.
  CPC ............. *A61B 5/063* (2013.01); *A61B 5/6885* (2013.01); *A61B 2562/06* (2013.01)

(56) References Cited

U.S. PATENT DOCUMENTS

| | | |
|---|---|---|
| 6,663,622 B1 | 12/2003 | Foley et al. |
| 6,711,439 B1 | 3/2004 | Bradley et al. |
| 8,880,160 B2 | 11/2014 | Shome et al. |
| 9,186,081 B2 | 11/2015 | Afonso et al. |
| 9,380,953 B2 | 7/2016 | Houben et al. |
| 2011/0137369 A1 | 6/2011 | Ryu |
| 2015/0208938 A1 | 7/2015 | Houben et al. |

OTHER PUBLICATIONS

Nayyar, Sachin, M.D., D.M., et al., "High-Density Mapping of Ventricular Scar A Comparison of Ventricular Tachycardia (VT) Supporting Channels With Channels That Do Not Support VT", Circ. Arrhythm Electrophysiol., Feb. 2014, pp. 90-98, vol. 7, (1).

Stiles, Martin K., et al., "Paroxysmal Lone Atrial Fibrillation Is Associated With an Abnormal Atrial Substrate", Journal of the American College of Cardiology, Apr. 7, 2009, pp. 1182-1191, vol. 53, No. 14.

Verma, Atul, M.D., et al., "Pre-Existent Left Atrial Scarring in Patients Undergoing Pulmonary Vein Antrum Isolation", Journal of the American College of Cardiology, Jan. 18, 2005, pp. 285-292, vol. 45, No. 2.

Haddad, Milad El, "Signal processing of intracardiac electrograms: optimization of mapping and ablation in tachyaarrhythmias", Ghent University—Curriculum Vitae, Jan. 1, 2014, pp. 1-190.

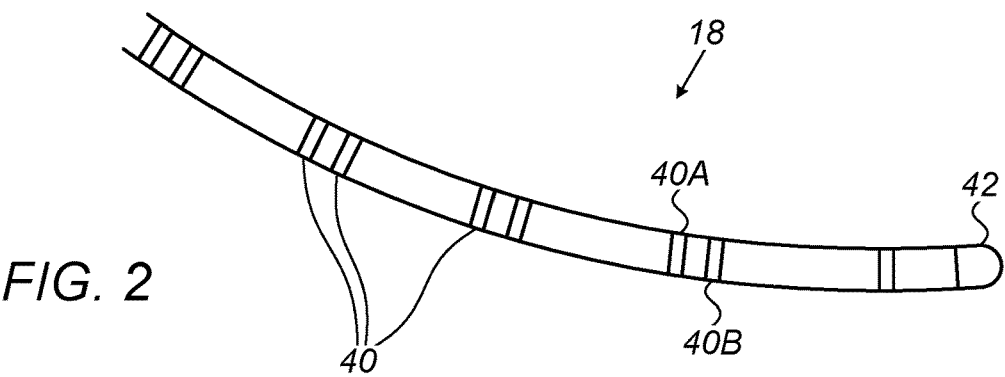
FIG. 2
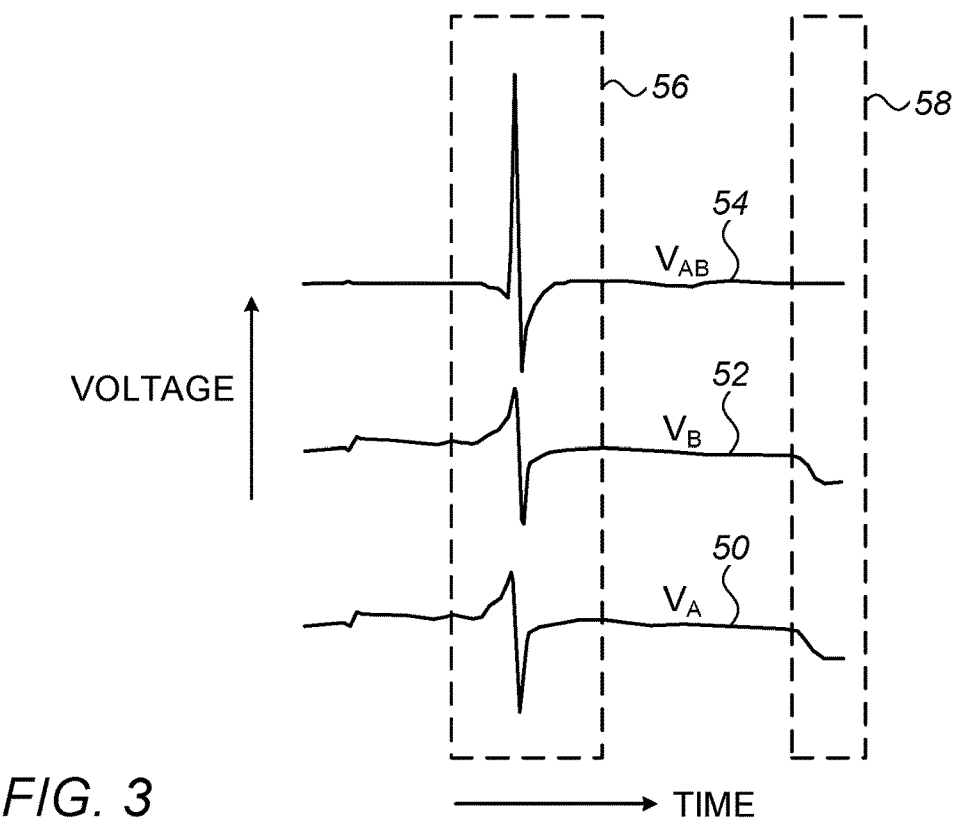
FIG. 3
FIG. 4
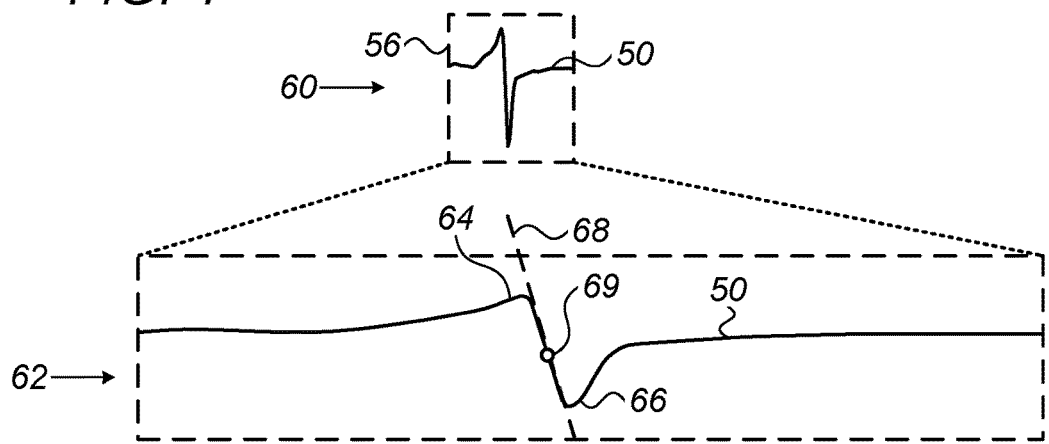

TISSUE CONDUCTION VELOCITY

CROSS REFERENCE TO RELATED APPLICATION

The present application is a continuation application of U.S. patent application Ser. No. 15/477,731 filed on Apr. 3, 2017.

FIELD OF THE INVENTION

The present invention relates generally to electrophysiological measurements, and particularly to measuring the conduction velocity in cardiac tissue.

BACKGROUND

In a typical atrial fibrillation procedure, the conduction velocity (CV) of an electrical impulse is an important parameter that can provide information to the clinician about the state of the tissue being ablated.

U.S. Pat. No. 6,711,439, which is incorporated herein by reference, describes how modern implantable cardiac stimulation devices include processing and data storage capabilities that may be exploited to track myocardial condition and autonomic tone.

U.S. Pat. No. 6,301,496, which is incorporated herein by reference, describes a method of diagnosing an abnormal condition in a biological structure, such as the heart, including the steps of measuring a physiological response at at least three sampled points on a surface of the biological structure, calculating a vector function related to the response, displaying a representation of the vector function, and inferring the abnormal condition from the representation.

U.S. Pat. No. 6,236,883, which is incorporated herein by reference, describes a method comprising the steps of identifying and localizing reentrant circuits from electrogram features using feature detection and localization (FDL) algorithms.

U.S. Pat. No. 8,880,160, which is incorporated herein by reference, describes a system which comprises a cardiac signal sensing and a processing circuit. The cardiac signal sensing circuit senses a first cardiac signal segment that includes a QRS complex and a second cardiac signal segment that includes a fiducial indicative of local ventricular activation.

U.S. Patent Application 2011/0137369, which is incorporated herein by reference, describes an exemplary method for optimizing pacing configuration. The method includes providing distances between electrodes of a series of three or more ventricular electrodes associated with a ventricle and selecting a ventricular electrode from the series.

U.S. Pat. No. 9,186,081, which is incorporated herein by reference, describes a system for diagnosing arrhythmias and directing catheter therapies. The system may allow for measuring, classifying, analyzing, and mapping spatial electrophysiological (EP) patterns within a body.

U.S. Pat. No. 6,663,622, which is incorporated herein by reference, describes devices and a method which are provided to assist a surgeon in ablating conduction paths in tissue, such as a heart. A device can be configured to operate as a template that adheres to the tissue surface, and allows the surgeon to more easily sever the conduction path to form a lesion in a desired location.

Commonly assigned U.S. Pat. No. 9,380,953, which is incorporated herein by reference, describes how a bipolar electrogram and a unipolar electrogram are recorded from electrodes of a probe, and differentiated with respect to time. Peaks are identified in the differentiated bipolar electrogram, and an activity window is defined that includes bipolar activity about the peaks. An extreme negative value in the differentiated unipolar electrogram within the activity window is reported as a unipolar activation onset. An annotation is selected from candidate minima in the differentiated unipolar electrogram within the activity window by excluding candidates that fail to correlate with activity in the bipolar electrogram.

Documents incorporated by reference in the present patent application are to be considered an integral part of the application except that, to the extent that any terms are defined in these incorporated documents in a manner that conflicts with definitions made explicitly or implicitly in the present specification, only the definitions in the present specification should be considered.

SUMMARY

Embodiments of the present invention that are described hereinbelow provide for an improved method for measuring conduction velocity in the heart of a living subject.

There is therefore provided, in accordance with an embodiment of the invention, a method which includes acquiring a bipolar signal from a first electrode and a second electrode contacting a first location and a second location, respectively, in a heart of a living subject, acquiring a unipolar signal from the first electrode while in contact with the first location, deriving from the bipolar signal and the unipolar signal a point in time at which the first location is generating the unipolar signal, and computing a metric for a conduction velocity of the unipolar signal at the first location based on a shape of the unipolar signal at the point in time.

In a disclosed embodiment, the first and second electrodes are located in a distal end of a catheter in the heart, and acquiring the bipolar signal includes verifying that the distal end is engaging tissue in the heart with a contact force no less than a preset minimum contact force. Additionally or alternatively, acquiring the bipolar signal includes verifying that the first and second electrodes are engaging tissue in the heart with an impedance to an electrode on a surface of the subject exceeding a preset minimum impedance.

In another embodiment, computing the metric includes finding a maximum value of an absolute value of a slope of the unipolar signal, and using the maximum value as the metric. Alternatively or additionally, computing the metric includes computing the metric based on a respective confidence level applied to at least one of the bipolar signal and the unipolar signal.

In yet another embodiment, the metric is accepted as valid when the point in time is within a window in time defined with reference to a signal acquired from the heart.

In an embodiment, the point in time occurs when a time-derivative of the unipolar signal reaches an extreme negative value.

In another embodiment, the metric of the conduction velocity is incorporated into a three-dimensional map of the heart.

There is also provided, in accordance with an embodiment of the invention, an apparatus which includes a first electrode and a second electrode respectively contacting a first location and a second location in a heart of a living subject and a processor which is configured to acquire a bipolar signal from the first electrode and the second electrode, acquire a unipolar signal from the first electrode while in contact with the first location, derive from the bipolar signal and the unipolar signal a point in time at which the first location is generating the unipolar signal, and compute a metric for a conduction velocity of the unipolar signal at the first location based on a shape of the unipolar signal at the point in time.

In an embodiment, the first and second electrodes are located in a distal end of a catheter in the heart, and acquiring the bipolar signal includes verifying that the distal end is engaging tissue in the heart with a contact force no less than a preset minimum contact force. Additionally or alternatively, acquiring the bipolar signal includes verifying that the first and second electrodes are engaging tissue in the heart with an impedance to an electrode on the surface of the subject no less than a preset minimum impedance.

In another embodiment, computing the metric includes finding a maximum value of an absolute value of a slope of the unipolar signal, and using the maximum value as the metric. Additionally or alternatively, computing the metric includes computing the metric based on a respective confidence level applied to at least one of the bipolar signal and the unipolar signal.

In yet another embodiment, the processor is configured to accept the metric as valid when the point in time is within a window in time defined with reference to a signal acquired from the heart.

In an embodiment, the point in time occurs when a time-derivative of the unipolar signal reaches an extreme negative value.

In another embodiment, the processor is configured to incorporate the metric of the conduction velocity into a three-dimensional map of the heart.

In yet another embodiment, the processor is configured to incorporate an indication of a goodness of contact of at least one of the first electrode and the second electrode with the heart into the map.

The present invention will be more fully understood from the following detailed description of the embodiments thereof, taken together with the drawings in which:

BRIEF DESCRIPTION OF THE DRAWINGS

FIG. 2 is a pictorial illustration of the distal end of a typical catheter, in accordance with a disclosed embodiment of the invention;

FIG. 3 is an illustration of typical electrophysiological signals as received by a processor from electrodes of the distal end as a function of time, in accordance with a disclosed embodiment of the invention;

FIG. 4 illustrates the extraction of a metric for conduction velocity from a unipolar signal, in accordance with a disclosed embodiment of the invention;

DETAILED DESCRIPTION OF EMBODIMENTS

Overview

Figure 1:
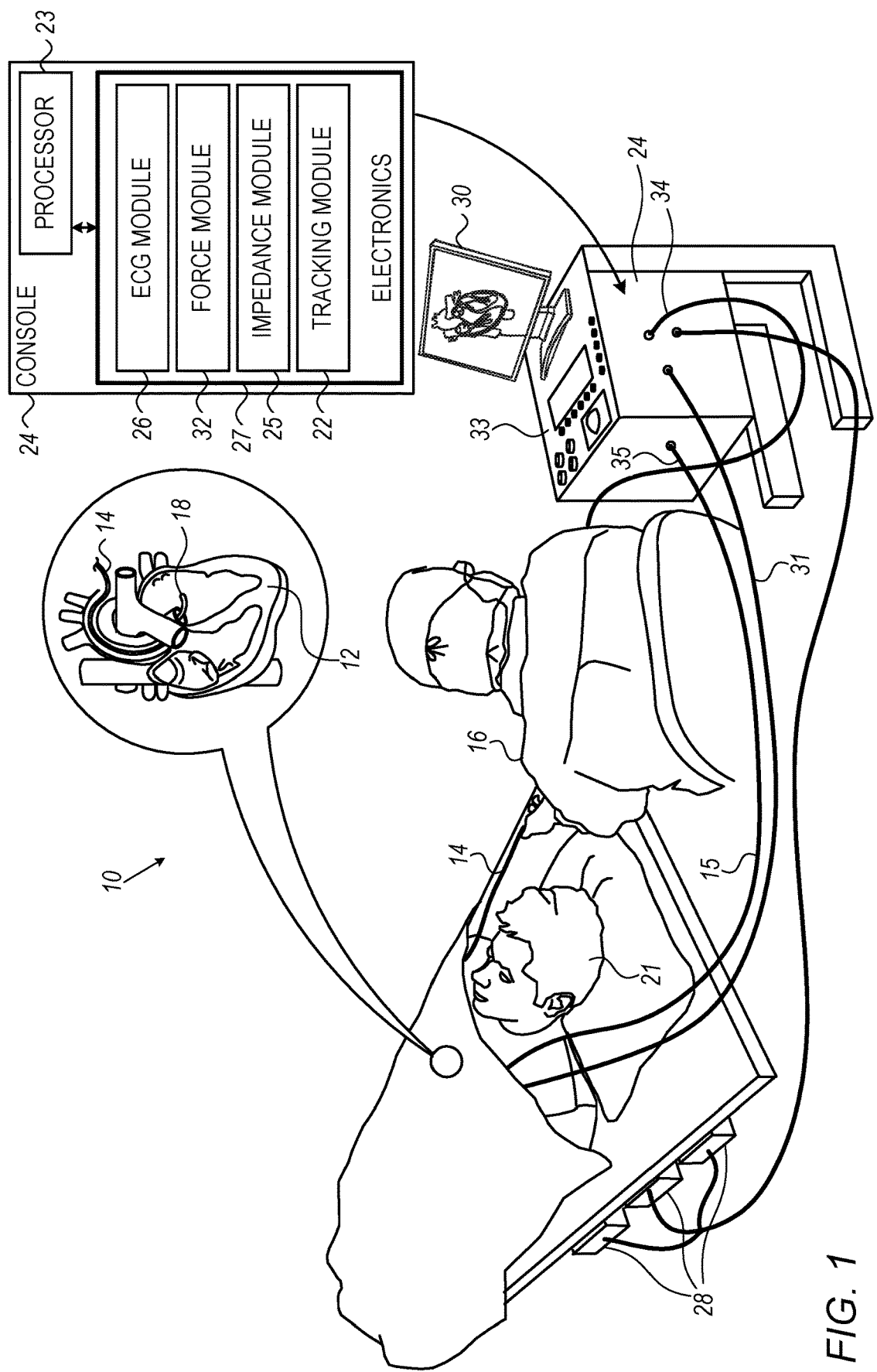
FIG. 1 is a pictorial illustration of an apparatus for mapping conduction velocity in a heart of a living subject, in accordance with a disclosed embodiment of the invention.

In a typical atrial fibrillation procedure, the conduction velocity (CV) of an electrophysiological signal in the heart of a subject is an important parameter that can provide information to the clinician about the state of the tissue being ablated. The conduction velocity in the heart typically ranges from 0.05 m/s in the sinoatrial (SA) node and atrioventricular (AV) node to 4 m/s in the Purkinje system. The conduction velocity in scar tissue is generally lower than in un-scarred tissue. The current method of estimating the conduction velocity is based on a measurement of the propagation time of an electrophysiological signal between two discrete points in the tissue. The signals are received from a probe with multiple electrodes, with the probe inserted into the heart so that the electrodes contact the cardiac tissue.

By using two of the electrodes to receive signals propagating in the cardiac tissue, an estimate for conduction velocity is obtained by dividing the estimated distance in the tissue between the two electrodes by the difference between the times of arrival of the signal at the two electrodes. The times of arrival are determined by, for example, so-called annotation points in the two signals, with an annotation point typically indicating the point in time where the time-derivative of the signal reaches an extreme negative value. This estimate for conduction velocity suffers from inaccuracies described in the following four points:

1. The location of each of the two electrodes is determined with a finite accuracy, which depends on the accuracy of the mapping system as well as on the deformation of the cardiac tissue due to the force exerted on it by the catheter. The relative impact of the finite accuracy on the estimate for the conduction velocity is significant when the separation between the two electrodes is small, typically a few millimeters.
2. The estimate for the conduction velocity gives an average conduction velocity over the separation between the two electrodes, lowering the spatial resolution of the mapping of the conduction velocity to that of the separation between the electrodes.
3. The separation between the electrodes does not necessarily give the actual path length between the electrodes, as the cardiac tissue may not be flat between the electrodes. An estimate for the path length is given by a reconstruction of the shape of the cardiac tissue based on spatial probing. Errors in this estimate may impact the accuracy of the path length, and subsequently the determination of the conduction velocity. Increasing the electrode separation to reduce the relative impact of the electrode location inaccuracy (point 1, above) will lower the spatial resolution (point 2, above) as well as increase the uncertainty of the actual path length (current point).
4. The time difference between the arrival times at the two electrodes is due to the actual magnitude of the velocity of the signal between the two electrodes only in the case where the local vector of propagation of the signal is collinear with the line connecting the two electrodes. Otherwise, the measured conduction velocity (derived from the measured time difference) is the actual conduction velocity multiplied by the cosine of the angle between the propagation vector and the line connecting the two electrodes.

5. If the annotation is done manually or automatically using a measure that is sensitive to noise, such as the maximum value of the bipolar signal, the noise-induced shift of the signal may further contribute to the error in the estimated conduction velocity.

Embodiments of the present invention that are described herein solve the above described problems by extracting a localized measure of the conduction velocity, based on the signal from a single electrode. The embodiments utilize both unipolar and bipolar signals received from the cardiac tissue.

In the embodiments of the present invention, two electrodes, respectively contacting a first location and a second location of cardiac tissue in a heart of a living subject, are used for acquiring a bipolar signal. A unipolar signal is acquired from the first electrode while it is in contact with the first location, and from the bipolar signal and the unipolar signal a point in time, at which the first location is generating the unipolar signal, is derived. Based on a shape of the unipolar signal at the point in time, a metric for the conduction velocity at the first location is computed.

SYSTEM DESCRIPTION

FIG. 1 is a pictorial illustration of an apparatus 10 for mapping conduction velocity in a heart 12 of a living subject 21, in accordance with a disclosed embodiment of the invention. Apparatus 10 comprises a probe, typically a catheter 14, which is percutaneously inserted by an operator 16, who is typically a physician, through the vascular system of subject 21 into a chamber or vascular structure of heart 12. Operator 16 brings a distal end 18 of catheter 14 into contact with the cardiac tissue at a target site for the measurement. Unipolar and bipolar electrophysiological signals are acquired using electrodes (shown in FIG. 2) on distal end 18. A metric for conduction velocity based on the electrophysiological signals is then calculated, and a map of conduction velocity is generated, according to the method disclosed below.

An additional probe, a reference catheter 15, is percutaneously inserted by operator 16 through the vascular system of subject 21. Operator 16 brings an electrode at the distal end (not shown) of reference catheter 15 into contact with a coronary sinus of subject 21. Reference catheter 15 is typically left in place for the duration of the conduction velocity mapping procedure; its function is to pace the heart either by an electrical timing pulse into the coronary sinus through a command from operator 16, and/or by a reference timing signal from the coronary sinus.

Apparatus 10 is controlled by a processor 23, which is located in a console 24. Processor 23 may comprise a general purpose or embedded computer processor, which is programmed with suitable software for carrying out the functions described hereinbelow. The software may be provided to processor 23 on tangible non-transitory media, such as CD-ROM (Compact Disc Read-Only Memory) or non-volatile memory. Alternatively or additionally, the apparatus 10 may comprise a digital signal processor or hard-wired logic.

Processor 23 communicates with electronics 27, which has a number of modules used by the processor to operate the apparatus. Thus, electronics 27 comprises modules such as an ECG (electrocardiography) module 26 for acquiring electrophysiological signals received from the electrodes at distal end 18, a force module 32 for evaluating the forces on the distal end, a tracking module 22 for determining the location and orientation of the distal end, and an impedance module 25 for measuring the impedance between the electrodes at the distal end and a patch on the body of subject 21. The modules may comprise hardware as well as software elements. Electronics 27 are located in console 24. Console 24 typically comprises a display 30 and controls 33 for the use of operator 16. Proximal ends 35 of, respectively, catheter 14 and reference catheter 15 are connected to console 24 and further to the modules of electronics 27.

For determining the position and orientation of distal end 18, apparatus 10 typically comprises a set of external radiators, such as field generating coils 28, which are located in fixed, known positions external to subject 21. Coils 28 generate electromagnetic fields in the vicinity of heart 12, and the fields are sensed by magnetic field sensors (not shown) located in distal end 18 and/or patches on the body of subject 21. The signals from the magnetic field sensors are transmitted to tracking module 22, and enable processor 23 and tracking module 22 to determine the position and orientation of distal end 18.

In order to provide data on the contact forces exerted by distal end 18 on the cardiac tissue, in some embodiments of catheter 14 the distal end also comprises contact force sensors (not shown) that provide signals to force module 32.

Body surface electrodes (not shown) are attached to the skin of subject 21 for providing an indifferent electrode as well as for acquiring additional electrophysiological signals. The body surface electrodes are connected via a cable 31 to console 24 and further to impedance module 25 and to ECG module 26.

One system that embodies the above-described features of apparatus 10 is the CARTO® 3 System, available from Biosense Webster, Inc., 3333 Diamond Canyon Road, Diamond Bar, Calif. 91765, USA. This system may be modified by those skilled in the art to embody the principles of the invention described herein.

FIG. 2 is a pictorial illustration of distal end 18 of catheter 14, in accordance with a disclosed embodiment of the invention. Distal end 18 comprises, by way of example, ring electrodes 40 and a tip electrode 42, with a disclosed embodiment having nine ring electrodes arranged at alternating intervals of 2 mm and 8 mm along the distal end. Operator 16 selects two of the electrodes, typically an adjacent pair of ring electrodes 40, or tip electrode 42 and the closest ring electrode 40, for acquiring two electrophysiological signals from which the bipolar and unipolar signals referred to above are received. Although FIG. 2 shows distal end 18 of single catheter 14 with ring electrodes 40 and tip electrode 42, other embodiments of the present invention may use alternative catheters with other types, numbers and configurations of electrodes.

In the following, for clarity the two electrodes selected by operator 16 are assumed to be a pair of ring electrodes 40, and are referred to as ring electrodes 40A and 40B. Alternatively, any other configuration between two different catheters or electrodes on different splines can be as well used.

Multi-electrode catheters that are suitable for acquiring unipolar and bipolar electrophysiological signals, and that also comprise distal end force and magnetic field sensors, are known in the art. An example of such a catheter is the THERMOCOOL SMARTTOUCH® Catheter, available from Biosense Webster, Inc.

FIG. 3 is an illustration of typical electrophysiological signals 50, 52, and 54 as a function of time, as received by processor 23 from ring electrodes 40A and 40B of distal end 18, in accordance with a disclosed embodiment of the invention. Signals 50 and 52 are unipolar signals with voltages $V_A$ and $V_B$, received from ring electrodes 40A and 40B, respectively, measured against the indifferent electrode. Processor 23 calculates bipolar signal 54 as the difference between unipolar signals 52 and 50 as a voltage $V_{AB}=V_B-V_A$. Typical peak-to-peak amplitudes of the signals are 0.05 mv to a few mV for unipolar signals 50 and 52, and range from 0.05 mv to a few mV for bipolar signal 54.

Two windows of time, a window 56 and a window 58, are marked in FIG. 3. In window 56, unipolar signals 50 and 52 originate from a local electrophysiological wave in the cardiac tissue and are acquired by ring electrodes 40A and 40B. Due to the differences in time at which the wave passes ring electrodes 40A and 40B, the resulting bipolar signal 54 has clear non-zero features and non-zero time derivatives within window 56. On the other hand, in window 58, unipolar signals 50 and 52 originate only from one or more non-local signals. As the non-local signals arrive at ring electrodes 40A and 40B at the same time, they are a common-mode signal for the two electrodes, and the subtraction of unipolar signals 50 and 52 yields a substantially zero bipolar signal 54 within window 58. This behavior of bipolar signal 54 in window 58, as opposed to varying bipolar signal 54 in window 56, is utilized for identifying in one of unipolar signals 50 and 52 the part which is due to a local signal.

FIG. 4 illustrates the extraction of a metric for the conduction velocity from unipolar signal 50, in accordance with a disclosed embodiment of the invention. A view 60 shows unipolar signal 50 within window 56, i.e. the part which is due to a local signal. For clarity, view 60 is stretched along the axis of time (horizontal axis) to a view 62. The conduction velocity of the electrophysiological signal passing under ring electrode 40A affects the temporal behavior of unipolar signal 50: the faster the electrophysiological signal passing under ring electrode 40A, the larger the change of unipolar signal 50 as a function of time. Based on this behavior of unipolar signal 50, its time-derivatives at so-called annotation points are used as candidates for a metric for the conduction velocity.

In the disclosure and in the claims, an annotation point corresponds to an inflection point of a unipolar signal that passes given criteria. The criteria, as well as the selection of the metric for the conduction velocity, are detailed in the description of the flowchart of FIG. 5.

For the sake of clarity, FIG. 4 illustrates a signal 50 which has only one inflection point 69 that qualifies as an annotation point. (In general, several inflection points may be recorded.) Inflection point 69 is selected as an annotation point for the following reasons:
  a) It is a well-defined point in time within unipolar signal 50, and
  b) At this point in time the time-derivative of the signal reaches an extreme negative value.

In embodiments of the present invention processor 23 calculates a metric of the conduction velocity based on the shape of the unipolar signal, which in a disclosed embodiment described hereinbelow is quantified as the absolute value of the time-derivative $$\frac{dV_A}{dt}$$

of unipolar signal 50 at a point in time comprising inflection point 69. This calculation is illustrated in FIG. 4, where the time-derivative 68 (marked with a dotted line as a slope) of unipolar signal 50 at inflection point 69, between a positive peak 64 and a negative peak 66, represents the metric for the conduction velocity. The metric of the conduction velocity is best described by the slope at inflection point 69, which can be calculated from unipolar signal 50, after removal of low pass components (as described in a pre-processing step 78 in FIG. 5), but other methods that are based on an average of the slope or a trend between positive peak 64 and negative peak 66 can equally be employed.

As the metric for the conduction velocity is measured for a single electrode (such as electrode 40A in the above example), the spatial resolution for the measurement is determined by the spatial extent of the contact between the single electrode and the cardiac tissue. A typical contact size is 1-2 mm. Reducing the size of the contact further by, for instance, reducing the size of electrode 40A yields the following additional advantages for the measurement of the metric for conduction velocity:
  1. It improves the spatial resolution of the measurement (i.e. it makes it "finer"), and
  2. It increases the absolute value of the time-derivative $$\frac{dV_A}{dt}$$

of unipolar signal 50 by reducing the spatial averaging effect as the measured potential is affected less by traveling electrophysiological waves that are originated further away.

Figure 5:
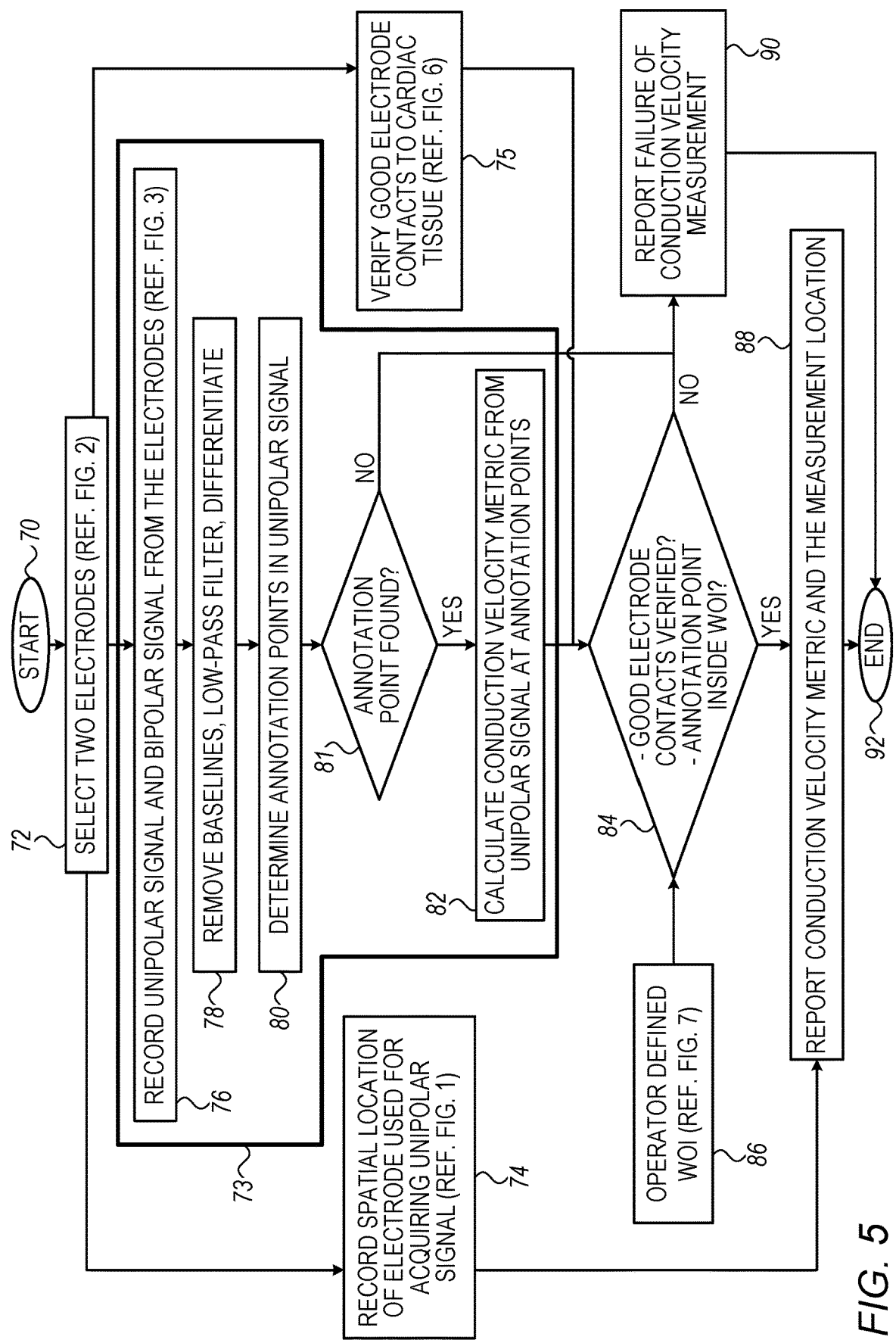
FIG. 5 is a flowchart of the steps that the processor implements for measuring a metric for conduction velocity at a known spatial point in the cardiac tissue of the heart, in accordance with a disclosed embodiment of the invention.

FIG. 5 is a flowchart of the steps that processor 23 implements for measuring a metric for conduction velocity at a known spatial point on the cardiac tissue, in accordance with a disclosed embodiment of the invention.

Processor 23 starts the measurement in a starting step 70, after which operator 16 selects two electrodes 40 of distal end 18 of catheter 14 in an electrode selection step 72. Referring to FIG. 2, operator 16 selects electrodes 40A and 40B, but alternative selections are equally possible. For clarity, in the following description the processor is assumed to measure the conduction velocity of the electrophysiological signal acquired by electrode 40A.

Returning to electrode selection step 72 of the flowchart of FIG. 5, once operator 16 has selected electrodes 40A and 40B, processor 23 runs three steps 73, 74, and 75, with all three steps starting at electrode selection step 72 and utilizing the selected electrodes 40A and 40B:
  1. In a conduction velocity metric step 73 processor 23 calculates a conduction velocity metric, as is detailed below;
  2. In a tracking step 74 processor 23 records the spatial location and orientation of electrode 40A as described in FIG. 1;
  3. In an electrode contact verification step 75 processor 23 verifies that the contact that electrodes 40A and 40B form with the cardiac tissue is sufficient, as is detailed below and in FIG. 6.

Processor 23 runs steps 73, 74, and 75 in parallel, as illustrated in the flowchart. Alternatively, processor 23 may run steps 73, 74, and 75 in a serial manner, or in any combination of parallel and serial manner.

We now describe in further detail the internal steps that conduction velocity metric step 73 comprises. In a recording step 76 processor 23 acquires and records unipolar signals 50 and 52 from, respectively, electrodes 40A and 40B, measured with respect to the indifferent electrode, and calculates bipolar signal 54 as the difference between unipolar signals 50 and 52.

In pre-processing step 78 processor 23 removes from each of signals 50 and 54 a baseline signal arising typically from movement of catheter 14, movement and respiration of subject 21, and/or other slowly varying far field signals. In a disclosed embodiment processor 23 first applies a median filter to signals 50 and 54 in order to remove the electrophysiological signals. Processor 23 further low-pass filters the resulting signals in order to smooth out edges resulting from the median filter and in order to reduce the amplification of noise by the subsequent differentiation. Other methods of baseline wander removal can be used, such fixed high-pass filtering or adaptive filtering. Alternatively, multiple activations from a saved spatial location can be averaged together and used for velocity calculation. The signals resulting from the low-pass filtering are estimates of the baseline signals for signals 50 and 54, and processor 23 subtracts these estimates from respective signals 50 and 54, producing baseline-corrected signals, herein referred to as unipolar signal 50B and bipolar signal 54B. Processor completes pre-processing step 78 by differentiating baseline-corrected signals 50B and 54B.

In an annotation step 80 processor 23 determines possible annotation points of unipolar signal 50B. In a disclosed embodiment the processor performs the determination by the following procedure:

1. Processor 23 locates (referring to FIG. 4) all inflection points 69 of unipolar signal 50B.
2. At the time defined by each inflection point 69, processor 23 tests for the following conditions:
   a. Is the time-derivative of bipolar signal 54B lower (more negative) than a predefined bipolar slope threshold? In a disclosed embodiment the threshold is set at −0.008 mV/ms.
   b. Is the absolute value of the ratio of the time-derivatives of bipolar signal 54B and unipolar signal 50B greater than a predefined ratio threshold? In a disclosed embodiment the threshold is set at 0.2.
   c. Is the time-derivative of unipolar signal 50B lower (more negative) than a predefined unipolar slope threshold? In a disclosed embodiment the threshold is set at −0.01 mV/ms.
3. In a time window around inflection point 69, processor 23 tests for the following condition:
   a. Are the peak-to-peak values of unipolar signal 50B and bipolar signal 54B above respective preset thresholds? In a disclosed embodiment the thresholds are typically in the range of 0.003-0.008 mV.

In a disclosed embodiment the time window is set as ±2 ms.

In some embodiments of the present invention, additional features of the signals are used. For example, such features can be the duration of the unipolar slope (from maximum to minimum), the amplitude of the unipolar signal in the time window from maximum to minimum, the amplitude of the bipolar window in that time window, the slope of the signals at the annotation point, as well as any relationship between these features. Each feature is compared against a predetermined fuzzy function that generates a score from 0 to 1. The higher the score the higher the likelihood that the activation is a true activation.

Since several features can be used, the final score from all features is either an arithmetic weighted mean (AWM) of individual scores, $$AWM = \frac{\sum_{1}^{N} w_i f_i}{\sum_{1}^{N} w_i},$$

where $w_i$ are predetermined weights and $f_i$ are individual scores, or a geometric weighted mean (GWM), GWM= $(\Pi_1^{Nf} w_i^{w_i})^{1/W}$ where $w_i$ are predetermined weights, $f_i$ are individual scores, and W is the sum of the weights. The final value is compared against specific threshold (for example 0.7 to 0.9) and only annotations passing this value are considered as valid annotation points.

In a comparison step 81, processor 23 checks whether all conditions 2a-c and 3a are satisfied and that at least one annotation point is found. If the result is positive, processor 23 moves on to a metric calculation step 82. If step 81 returns negative, processor 23 bypasses metric calculation step 82, a decision step 84, and a report step 88, and moves directly to failure report step 90.

In metric calculation step 82 processor 23 calculates the absolute value of the time-derivative $$\frac{dV_A}{dt}$$

of unipolar signal 50B at each inflection point 69, and reports it to decision step 84.

Figure 6:
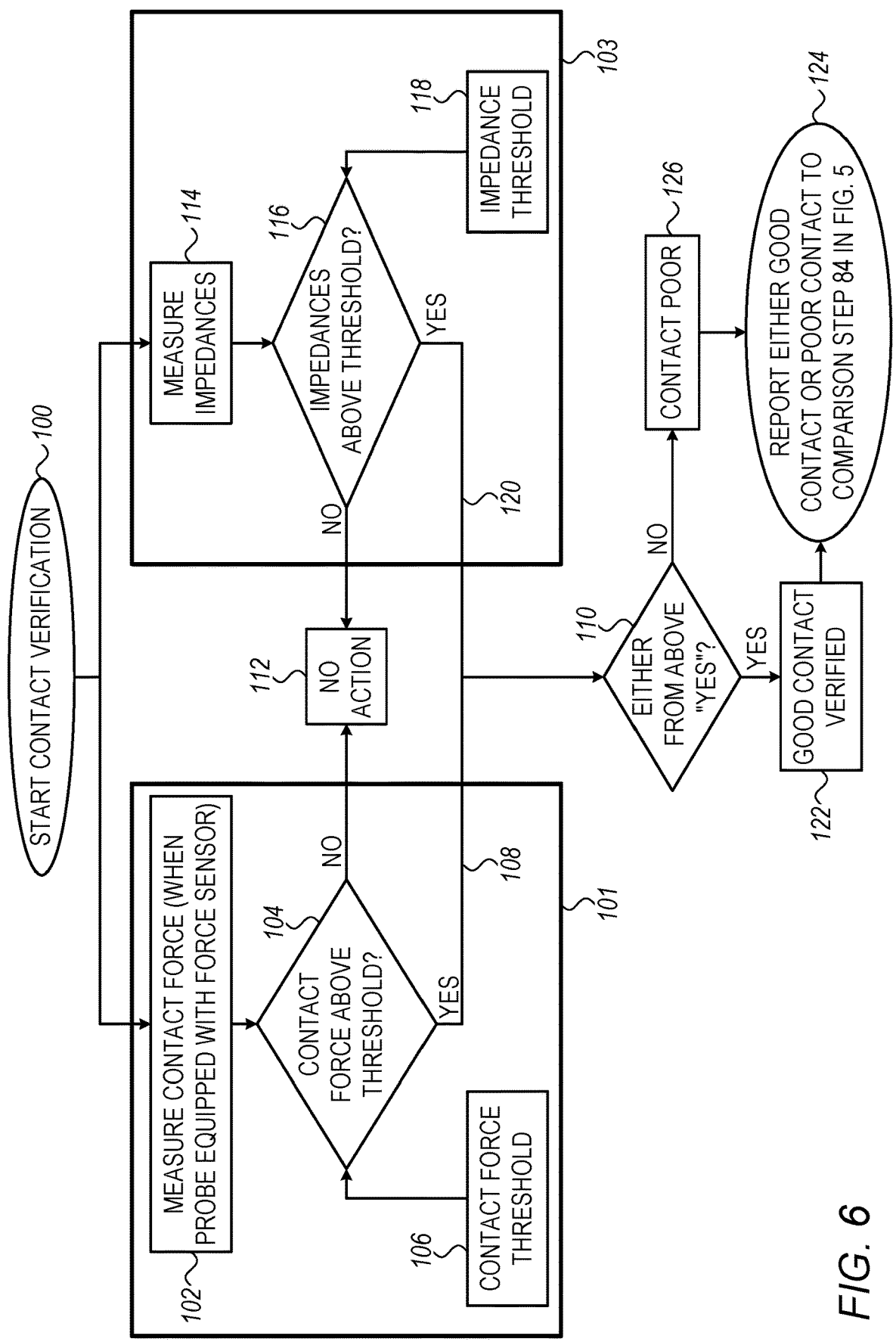
FIG. 6 is a flowchart of the steps that the processor implements for verifying a good contact between an electrode and the cardiac tissue of the heart, in accordance with a disclosed embodiment of the invention.

In electrode contact verification step 75 processor 23, as is further detailed with regard to FIG. 6, verifies whether electrodes 40A and 40B are in good contact with the cardiac tissue. Depending on the outcome of the verification process in contact verification step 75, processor reports to decision step 84 a message of either a "good contact" or a "poor contact".

In decision step 84, processor 23 checks whether a "good contact" message has been received from contact verification step 75. In some embodiments, processor 23 further checks whether the annotation point, where the conduction velocity metric was calculated in calculation step 82, is located within an operator-defined window of interest (WOI), generated in a WOI step 86, described with reference to FIG. 7. If a "good contact" message has been received, and the annotation point is within WOI, processor 23 reports in a report step 88 the conduction velocity metric calculated in metric calculation step 82 together with the location of electrode 40A recorded in tracking step 74. The process then ends in end step 92.

If in decision step 84, a "poor contact" message from contact verification step 75 has been received, or the annotation point is not within WOI, processor 23 reports a failure of contact velocity measurement in a failure reporting step 90, and the process ends in end step 92.

For each additional measurement location selected by operator 16, processor 23 stores the results for each successful measurement of the conduction velocity metric and the measurement location in its memory. At the request of operator 16, processor 23 generates a three-dimensional map of heart 12 incorporating conduction velocity metrics acquired across the measurement locations, and displays it on display 30.

In some embodiments, the map may incorporate respective indications of a goodness of contact of the electrodes. Thus, if a good contact message has been received, the processor may incorporate an indication of the good contact into the conduction velocity metric displayed on the map, and if a poor contact message is received, the processor may incorporate an indication of a poor contact into a corresponding region of the map.

Processor 23 may also, at a request by operator 16, store the map on a removable medium, send it to a printer if one is connected to the processor, or transmit it over electronic data lines to a location requested by the operator.

In FIGS. 3-5 the directions for rising and falling slopes are determined by the choice of polarity for the measurement of signals 50, 52, and 54. Processor 23 could alternatively measure any of these signals with opposite polarity, which would invert the signal and its slopes. The effect of these kinds of inversions will affect the logic and calculations in FIGS. 3-5 in a way that will be apparent to those having ordinary skill in the art.

FIG. 6 is a flowchart showing the steps within step 75 of FIG. 5 that processor 23 implements for verifying a good contact between, on the one hand electrodes 40A and 40B, and, on the other hand, the cardiac tissue, in accordance with a disclosed embodiment of the invention.

Unipolar signals 50 and 52 are typically accurate representations of the electrophysiological signals in the cardiac tissue at the locations of electrodes 40A and 40B. Any inaccuracy may lead to an inaccurate determination of the metric for the conduction velocity. In order to assure an accurate representation of the electrophysiological signals, there should be a good contact of electrodes 40A and 40B with the cardiac tissue. Processor 23 performs the contact verification process separately for both electrodes 40A and 40B.

Processor 23 starts the contact verification process in a starting step 100. Processor 23 runs two steps, a contact force verification step 101 and an impedance verification step 103. As illustrated in the flowchart, processor 23 runs steps 101 and 103 in parallel. Alternatively, processor 23 may run steps 101 and 103 in series. For verification of contact, alternative methods, such as those based on ultrasonic waves or light sources, may be used.

The internal steps that contact force verification step 101 comprises are as follows. In a force measurement step 102, processor 23, in conjunction with force module 32, measures the contact force of distal end 18 of catheter 14 against the cardiac tissue, provided that the distal end is equipped with a force sensor. In case distal end 18 is not equipped with such a force sensor, contact force verification step 101 is eliminated from the flowchart of FIG. 6. In a comparison step 104, processor 23 compares the results from the contact force measurements to a preset contact force threshold, received from a threshold step 106. In case both measured contact forces exceed the preset threshold, processor 23 sends a positive logic signal 108 to a comparison step 110. In case one or both of the measured contact forces are below the preset threshold, processor 23 takes no action as per a "no action" step 112.

Assessing the degree of contact of electrodes 40A and 40B to cardiac tissue is based on the fact the impedance measured to a patch on the body of patient 21 through cardiac tissue is higher than that measured through blood surrounding the electrodes. The internal steps that impedance verification step 103 comprises are as follows. In a impedance measurement step 114, processor 23 measures, utilizing impedance module 25, the impedance of each of the electrodes 40A and 40B with respect to a threshold received from an impedance threshold step 118. In impedance threshold step 118 the impedance threshold is calculated based on the location of electrodes 40A and 40B, and is of the order of 100Ω. When both impedances are above the preset threshold, this is taken as an indication that the impedance to the patch has been measured through cardiac tissue, and that electrodes 40A and 40B are in sufficient contact with the cardiac tissue, which leads to processor 23 sending a positive logic signal 120 to comparison step 110. In case one or both of the measured impedances are below the preset threshold, processor 23 takes no action as per "no action" step 112.

If at least one positive logic signal 108 or 120 is received by comparison step 110, processor 23 issues a verification message of good contact in a contact verification step 122, and a report step 124 sends a "good contact" message to comparison step 84 of FIG. 5. In case both contact verification step 101 and impedance verification step 103 have ended in "no action" step 112, step 110 receives no positive logic signals, processor 23 issues a message of poor contact in a contact failure step 126, and a report step 124 sends a "poor contact" message to comparison step 84 of FIG. 5.

Figure 7:
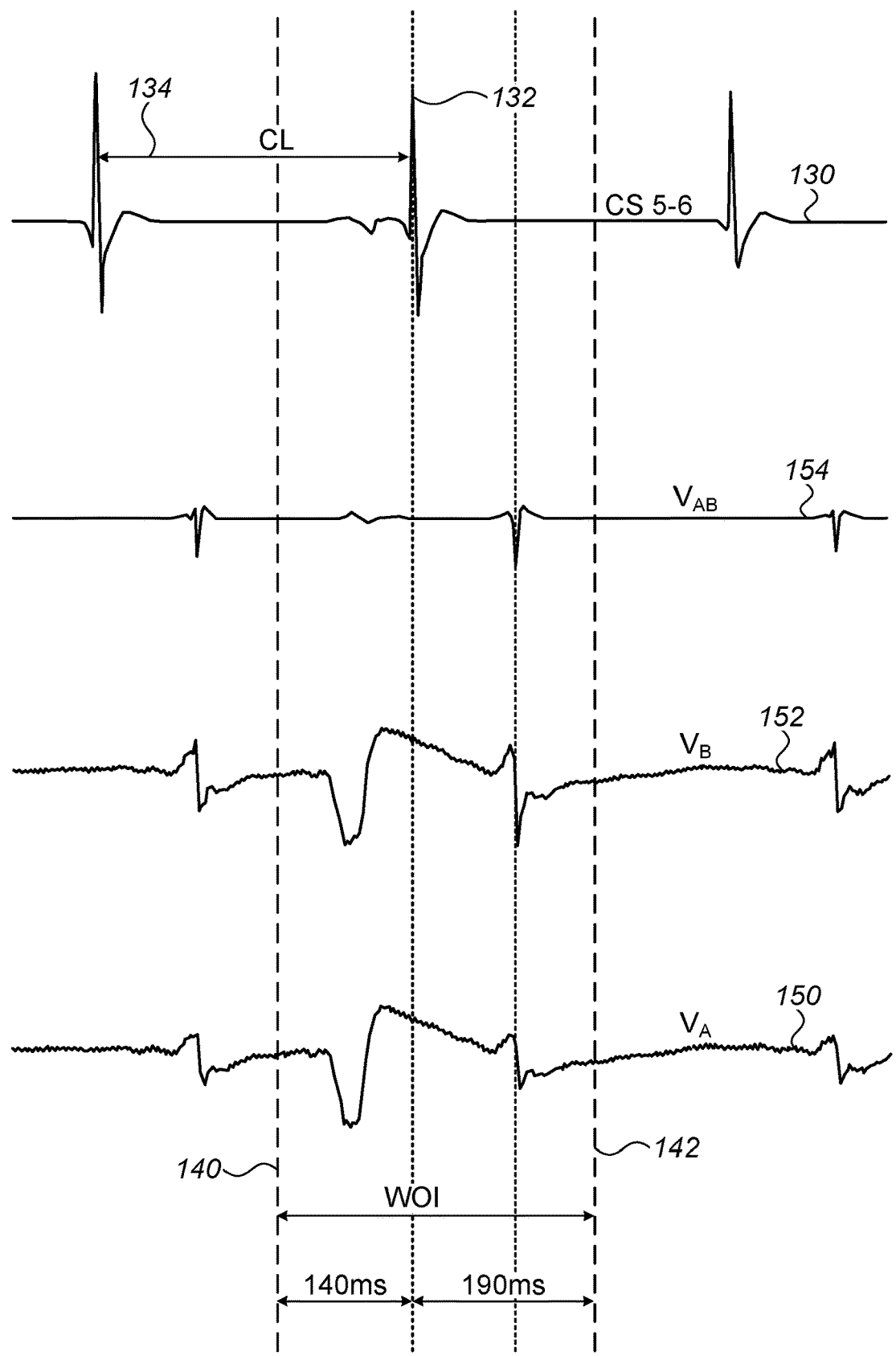
FIG. 7 illustrates how an operator defines a window of interest (WOI), in accordance with a disclosed embodiment of the invention.

FIG. 7 illustrates a typical example of how operator 16 defines the window of interest (WOI), in accordance with a disclosed embodiment of the invention. In an alternative embodiment, WOI may be defined by an automatic algorithm that takes into account the cycle length and/or the reference channels of the ECG while looking for a repetitive cycle. This is the WOI used in step 86 of FIG. 5. FIG. 7 displays a signal 130, which a signal CS 5-6 obtained from electrodes 5 and 6 from a stationary catheter in the coronary sinus of heart 12 of subject 21. FIG. 7 also displays a bipolar signal 154 and distal and proximal unipolar signals 152 and 150, respectively, similar to signals 54, 52, and 50 in FIG. 3. Operator 16 observes from signal 130 a peak 132 of the signal as well as a cycle length 134 (CL) of tachycardia, and determines the WOI around the peak based on the cycle length. In the disclosed embodiment, operator 16 defines a start point 140 of the WOI as 140 ms before peak 132, and an end point 142 of WOI as 190 ms after peak 132.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A method for measuring the conduction velocity in cardiac tissue, the method comprising a processor and associated circuitry for:
   acquiring a bipolar signal from a first electrode and a second electrode contacting a first location and a second location, respectively, in a heart of a living subject;
   acquiring a unipolar signal from the first electrode while in contact with the first location in cardiac tissue;
   deriving from the bipolar signal and the unipolar signal a point in time at which the first location is generating the unipolar signal;
   computing a metric for a conduction velocity of the unipolar signal at the first location based on a shape of the unipolar signal at the point in time; and
   incorporating the metric for a conduction velocity into a three-dimensional map of a heart of a living subject and displaying the image to a user on a display.

2. The method according to claim 1, wherein the first and second electrodes are located in a distal end of a catheter in the heart, and wherein acquiring the bipolar signal comprises verifying, when acquiring the signal, that the distal end is engaging tissue in the heart with a contact force no less than a preset minimum contact force.

3. The method according to claim 1, wherein acquiring the bipolar signal comprises verifying, when acquiring the signal, that the first and second electrodes are engaging tissue in the heart with an impedance to an electrode on a surface of the subject exceeding a preset minimum impedance.

4. The method according to claim 1, wherein computing the metric comprises finding a maximum value of an absolute value of a slope of the unipolar signal, and using the maximum value as the metric.

5. The method according to claim 1, wherein computing the metric comprises computing the metric based on a respective confidence level applied to at least one of the bipolar signal and the unipolar signal.

6. The method according to claim 1, and comprising accepting the metric as valid when the point in time is within a window in time defined with reference to a signal acquired from the heart.

7. The method according to claim 1, wherein the point in time occurs when a time-derivative of the unipolar signal reaches an extreme negative value.

8. The method according to claim 1, and comprising incorporating the metric of the conduction velocity into a three-dimensional map of the heart.

* * * * *